(12) United States Patent
Luthra et al.

(10) Patent No.: US 10,472,329 B2
(45) Date of Patent: Nov. 12, 2019

(54) PROCESS FOR THE PREPARATION OF INTERMEDIATES USEFUL IN THE SYNTHESIS OF ELUXADOLINE

(71) Applicant: ALLERGAN HOLDINGS UNLIMITED COMPANY, Dublin (IE)

(72) Inventors: Parven Kumar Luthra, Maharashtra (IN); Chandrasekhar Sinha, Maharashtra (IN); Syed Aziz Imam Quadri, Andhra Pradesh (IN); Tonmoy Chitta Das, Kolgata (IN)

(73) Assignee: Allergan Holdings Unlimited Company, Dublin (IE)

( * ) Notice: Subject to any disclaimer, the term of this patent is extended or adjusted under 35 U.S.C. 154(b) by 0 days.

(21) Appl. No.: 15/552,639

(22) PCT Filed: Feb. 22, 2016

(86) PCT No.: PCT/IS2016/050003
§ 371 (c)(1),
(2) Date: Aug. 22, 2017

(87) PCT Pub. No.: WO2016/135756
PCT Pub. Date: Sep. 1, 2016

(65) Prior Publication Data
US 2018/0029994 A1    Feb. 1, 2018

(30) Foreign Application Priority Data

Feb. 23, 2015  (IS) .............................................. 9062

(51) Int. Cl.
*C07D 233/64* (2006.01)
*C07C 55/07* (2006.01)

(52) U.S. Cl.
CPC ............ *C07D 233/64* (2013.01); *C07C 55/07* (2013.01); *C07B 2200/13* (2013.01)

(58) Field of Classification Search
CPC .................................................. C07D 233/64
See application file for complete search history.

(56) References Cited

U.S. PATENT DOCUMENTS

| 7,741,356 B2 | 6/2010 | Breslin et al. |
| 2005/0038087 A1 | 2/2005 | Chabrier De Lassauniere et al. |
| 2006/0094708 A1 | 5/2006 | Qian et al. |
| 2006/0211861 A1 | 9/2006 | Cai et al. |

FOREIGN PATENT DOCUMENTS

| EP | 1 305 294 B1 | 4/2007 |
| WO | WO 2004/071448 A2 | 8/2004 |
| WO | WO 2006/002236 A1 | 1/2006 |
| WO | WO 2013/061205 A2 | 5/2013 |

OTHER PUBLICATIONS

PubChem CID 51715957, National Center for Biotechnology Information. PubChem Compound Database; CID=51715957, https://pubchem.ncbi.nlm.nih.gov/compound/51715957 (accessed Jul. 12, 2018), create date May 20, 2011 (Year: 2011).*
International Search Report and Written Opinion prepared by the European Patent Office dated Apr. 12, 2016, for International Application No. PCT/IS2016/050003.
Search Report prepared by the Danish Patent and Trademark Office for Application No. SE 2015 00569.
Breslin, H.J. et al.: "Identification of a dual δ OR antagonist/μ OR agonist as a potential therapeutic for diarrhea-predominant Irretable Bowel Syndrome (IBS-d)" Bioorganic & Medicinal Chemistry Letters, 2012, vol. 22, pp. 4869-4872.

* cited by examiner

*Primary Examiner* — Laura L Stockton
(74) *Attorney, Agent, or Firm* — Andrew Chien

(57) ABSTRACT

The invention relates to an improved process for preparing [(S)-1-(4-phenyl-1-H-imidazol-2-yl)-ethyl]-amine. The process involves formation of the novel intermediate crystalline compound [(S)-1-(4-phenyl-1-H-imidazol-2-yl)-ethyl]-carbamic acid tert-butyl ester oxalate.

4 Claims, 4 Drawing Sheets

PROCESS FOR THE PREPARATION OF INTERMEDIATES USEFUL IN THE SYNTHESIS OF ELUXADOLINE

This application is a national stage application under 35 U.S.C. 371 and claims the benefit of PCT Application No. PCT/IS2016/050003 having an international filing date of 22 Feb. 2016, which designated the United States, which PCT application claimed the benefit of Iceland Patent Application No. 9062 filed 23 Feb. 2015.

BACKGROUND OF THE INVENTION

Eluxadoline is a mixed μ-opioid receptor agonist δ-opioid receptor antagonist that has been developed for treatment of diarrhea-predominant irritable bowel syndrome. Compound of formula II is an intermediate in a process of synthesis of Eluxadoline, as described in U.S. Pat. No. 7,741,356.

The compound with formula (II) when prepared according to the process disclosed in U.S. Pat. No. 7,741,356 requires purification by column chromatography, which reduces overall yield. Moreover, the process is not amenable to large scale synthesis.

The present invention provides a process that overcomes these drawbacks. Thus, the invention relates to a novel method of preparing compound of formula (II), that results in a compound of high purity and yield. The invention also relates to a novel intermediate in the synthesis of compound of formula (II).

SUMMARY OF THE INVENTION

The present invention relates in one aspect to the acid salt of a compound with the formula

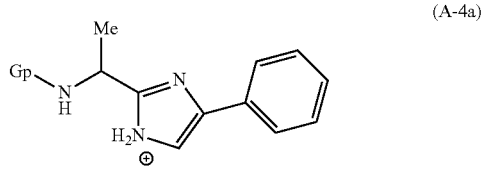

wherein Gp is an amino protecting group. In a preferred embodiment, the compound is an oxalate salt. The invention further relates to the crystalline compound [(S)-1-(4-phenyl-1-H-imidazol-2-yl)-ethyl]-carbamic acid tert-butyl ester oxalate. The compound, when obtained by the process disclosed herein, has the distinct and unique advantage of being obtainable in high yield and very high purity by the disclosed process.

Another aspect of the invention relates to a process of preparing [(S)-1-(4-phenyl-1-H-imidazol-2-yl)-ethyl]-amine of formula (II) by the following scheme:

Scheme I:

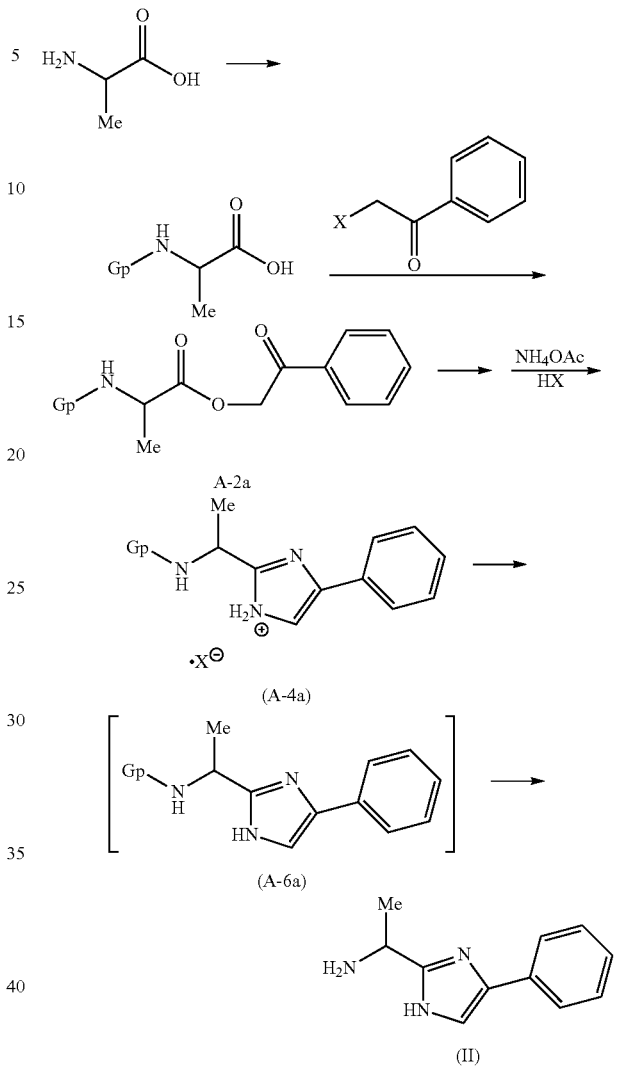

Wherein Gp is an amino protecting group, HX is any organic or inorganic acid, and X⁻ is the anion of the corresponding organic or inorganic acid salt.

The process comprises steps of
a) Treating L-alanine with an amino protecting group to obtain an amino protected L-alanine;
b) Reacting the amino protected L-alanine with phenacyl chloride to obtain compound of formula (A-2a);
c) Treating compound of formula (A-2a) with ammonium acetate to form an amino protected (S)-1-(4-phenyl-1-H-imidazol-2-yl)-ethanamine;
d) Treating the amino protected (S)-1-(4-phenyl-1-H-imidazol-2-yl)-ethanamine with a suitable acid to obtain an amino protected (S)-1-(4-phenyl-1-H-imidazol-2-yl)-ethanamine acid salt of formula (A-4a);
e) converting the amino protected (S)-1-(4-phenyl-1-H-imidazol-2-yl)-ethanamine acid salt of formula (A-4a) to amino protected (S)-1-(4-phenyl-1-H-imidazol-2-yl)-ethanamine by treatment with a base; and
f) deprotecting the amino protected (S)-1-(4-phenyl-1-H-imidazol-2-yl)-ethanamine to give (S)-1-(4-phenyl-1-H-imidazol-2-yl)-ethanamine of compound of formula (II).

In a preferred embodiment, the acid in step d) is oxalic acid, and the acid salt thus obtained is an oxalate salt of the compound of formula (A-4a). In a preferred embodiment, the amino protecting group is a tert-butyl ester group that is formed by reaction of L-alanine with di-tert-butoxycarbonyl anhydride.

The process can optionally include the further conversion of the compound of formula (II) to obtain eluxadoline by methods known in the art.

The invention also relates to a process for the preparation of a compound of formula

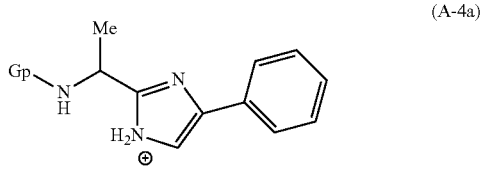

(A-4a)

comprising the steps of
a) Treating L-alanine with an amino protecting group to obtain an amino protected L-alanine;
b) Reacting the amino protected L-alanine with phenacyl chloride to obtain compound of formula (A-2a);
c) Treating compound of formula (A-2a) with ammonium acetate to form an amino protected (S)-1-(4-phenyl-1-H-imidazol-2-yl)-ethanamine;
d) Treating the amino protected (S)-1-(4-phenyl-1-H-imidazol-2-yl)-ethanamine with a suitable acid to obtain an amino protected (S)-1-(4-phenyl-1-H-imidazol-2-yl)-ethanamine acid salt of formula (A-4a);

Preferably, the amino protecting group is a tert-butyl ester group that is formed by reaction with di-tert-butoxycarbonyl anhydride.

The invention further relates to the oxalate salt of compound with formula (A-4a). In a preferred embodiment, the amino protecting group Gp the compound with formula (A-4a) is di-tert-butoxycarbonyl anhydride (Boc).

Further, the invention relates to crystalline [(S)-1-(4-phenyl-1-H-imidazol-2-yl)-ethyl]-carbamic acid tert-butyl ester oxalate. Preferably, the compound is characterized by at least one of
a. Powder X-ray diffraction peaks with 2-theta values of about 9.05, 10.66, 13.3, 14.69, 16.78, 19.0, 20.76, 21.64, 24.84 and 25.69°.
b. A differential scanning calorimetric thermogram with an endothermic peak at about 93° C.

It should be appreciated and is well known to the skilled person that the powder x-ray diffraction pattern can have 2-theta values that show a slight deviation from the above recited values. Thus in one embodiment, the compound is characterized by powder X-ray diffraction peaks with 2-theta values of 9.05, 10.66, 13.3, 14.69, 16.78, 19.0, 20.76, 21.64, 24.84 and 25.69+/−0.1°, which should be interpreted to mean that any of the values can deviate by up to 0.1° from the recited value. In another embodiment, the compound is characterized by a powder X-ray diffraction pattern with 2-theta values that comprise at least one, at least two, at least three, at least four, at least five, at least six, at least seven, at least eight, at least nine, or at least all 10 of the 2-theta values 9.05, 10.66, 13.3, 14.69, 16.78, 19.0, 20.76, 21.64, 24.84 and 25.69+/−0.1°.

Preferably, the [(S)-1-(4-phenyl-1-H-imidazol-2-yl)-ethyl]-carbamic acid tert-butyl ester oxalate obtained in step d) of the process of the invention is characterized by at least one of: X-ray diffraction peaks with 2-theta values of 9.05, 10.66, 13.3, 14.69, 16.78, 19.0, 20.76, 21.64, 24.84 and 25.69° and a differential scanning calorimetric thermogram with an endothermic peak at about 93° C.

DETAILED DESCRIPTION OF THE INVENTION

Figure 1:
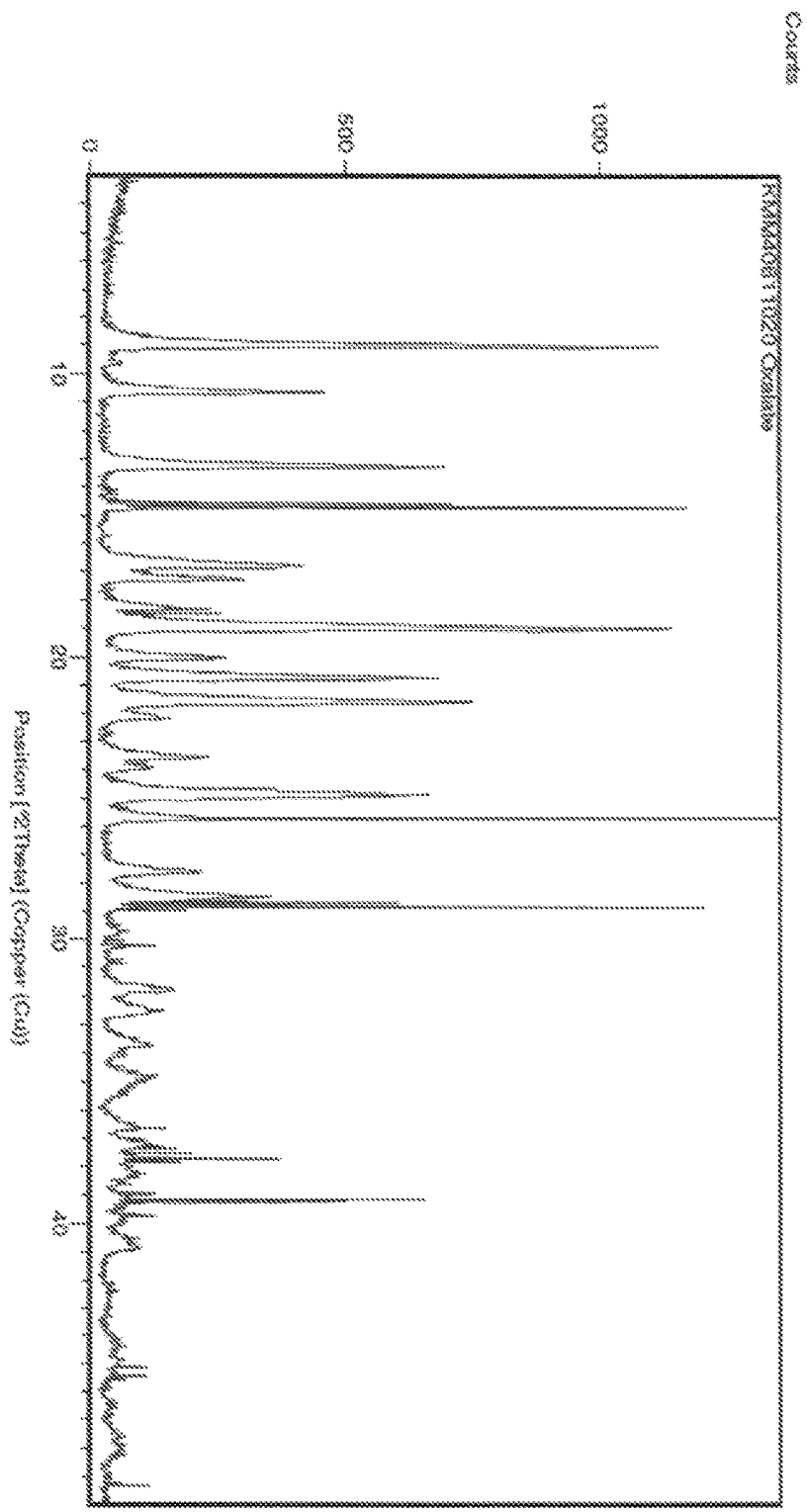
FIG. 1 shows structural analysis of [(S)-1-(4-phenyl-1-H-imidazol-2-yl)-ethyl]-carbamic acid tert-butyl ester oxalate by X-ray diffraction (XRD), as obtained by the process of the invention.

Before describing particular embodiments of the present invention, it is to be understood that the invention is not intended to be limited to the particular embodiments that are described in the following. It is also to be understood that the terminology used herein is for the purpose of describing particular embodiments, and is not intended to be limiting in any way.

It should be noted that as used herein, the singular forms "a," "an," and "the" include plural references unless the context clearly dictates otherwise. Thus, for example, reference to "a reagent" includes one or more of such different reagents and reference to "the method" includes reference to equivalent steps and methods known to those of ordinary skill in the art that could be modified or substituted for the methods described herein.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also contemplated, subject to any specifically excluded limit in the stated range. Where the stated range includes one or both of the limits, ranges excluding either or both of those included limits are also contemplated.

It should be understood that the particular methodology, protocols, material, reagents, and substances, etc., described herein can vary. Thus, variations that are within the skills of the ordinary practitioner are also contemplated. The terminology used herein is for the purpose of describing particular embodiments only, and is not intended to limit the scope of the present invention, which is defined by the claims.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

The present invention provides a novel process for preparing [(S)-1-(4-phenyl-1-H-imidazol-2-yl)-ethyl]-amine of formula (II). The process provides the distinct and unique advantage that the compound is obtained in high purity and yield, without the need for chromatographic purification, in a cost effective manner that is further adaptable for industrial scaling. The invention further provides the novel compound with formula (A-4a) that is formed in the process of preparing compound with formula (II).

In a preferred process according to the invention, L-alanine is first protected with a suitable amino protecting group. The amino protecting group can be any suitable protecting group known to the skilled person. For example, the amino protecting group can be any one of 9-fluorenylmethyl carbamate (FMOC amide), t-butyl carbamate (BOC amide), benzyl carbamate, acetamide, trifluoroacetamide, phtalimide, benzylamine, triphenylmethylamine, benzylideneamine, and tosylamide (see, e.g., T. W. Green, P. G. M. Wuts, *Protective Groups in Organic Synthesis*, Wiley-Interscience, New York, 1999). In a preferred embodiment, L-alanine is reacted with di-tert-butoxycarbonyl anhydride in a suitable solvent, such as a mixture of water and 1,4-dioxane, to obtain a Boc-protected L-alanine.

The amino-protected L-alanine is subsequently reacted with phenacyl chloride to obtain a compound of formula (A-2a). The latter step is preferably performed by reacting the protected S-alanine with potassium carbonate in DMF, prior to the addition of phenacyl chloride. This reaction has a distinct advantage over the prior art (e.g., Example 31 of US20040132788), in which cesium carbonate is first reacted with a protected amino acid in ethanol, which requires the use of expensive (cesium carbonate) and restricted (ethanol) reagents. Furthermore, by this prior art protocol, the ethanol solvent needs to be removed by evaporation prior to the reaction with phenacyl chloride.

The present invention overcomes this disadvantage by using potassium carbonate, and preferably performing the entire reaction in dimethyl formamide (DMF). A further advantage of the present invention is that the reaction with phenacyl chloride is complete in a considerably shorter time than the 16 hours described in US20040132788. The reaction with phenacyl chloride is preferably carried out over a time period of 3 to 6 hours at a temperature of about 20 to 50° C., and preferably in the range of about 20 to 40° C., and even more preferably in the range of about 20 to 30° C. The reaction is carried out in a polar solvent. Preferably, the solvent is tetrahydrofuran, acetone, acetonitrile, dimethylformamide, dimethylsulfoxide, isopropanol, or any C1-C4 aliphatic alcohol, or a mixture thereof. More preferably, the solvent is dimethylformide.

Compound A-2a is preferably obtained by extraction into a suitable solvent such as ethyl acetate, followed by recrystallization.

Compound of formula (A-2a) is on treatment with ammonium acetate converted to [(S)-1-(4-phenyl-1-H-imidazol-2-yl)-ethyl]-carbamic acid tert-butyl ester, which on treatment with oxalic acid gives oxalate salt of compound of formula (A-4a). An advantage of this method is the solid nature of oxalate salt which readily precipitates from the reaction solution. The advantage is that other unwanted impurities and/or reactants remain in mother liquor and separation of oxalate salt is easy by filtration. Preferably, the reaction with ammonium acetate is carried out in an apolar solvent, such as benzene, toluene, cyclohexane, pentane, hexane, chloroform and diethyl ether. More preferably, the solvent is toluene, and the reaction is preferably carried out at a temperature in the range of about 70 to 120° C., preferably in the range of about 80 to 110° C., more preferably in the range of about 90 to to 110° C., and even more preferably in the range of about 95 to 105° C. Following cooling, preferably to about 40 to 45° C., and addition of water, the organic layer is distilled, preferably at reduced pressure. The resulting residue is subsequently dissolved in a suitable polar solvent, such as THF, dichloromethane, diethyl ether or ethyl acetate. Preferably, the solvent is ethyl acetate. Oxalic acid, or another suitable acid, is added to the resulting solution, followed by stirring at an appropriate temperature, which is preferably about 0 to 5° C. Compound of formula (A-4a) is thus obtained as a crystalline salt. The compound (A-4a) is obtained in high yield and very high purity by this process.

The oxalate salt of compound (A-4a) is obtained as a solid material, which is a distinct advantage, as compared with a process that includes evaporation of solvent to obtain a solid compound. The crystals obtained by the method are preferably off-white in colour, the product (A-4a) being non-hygroscopic.

Compound (A-4a), [(S)-1-(4-phenyl-1-H-imidazol-2-yl)-ethyl]-carbamic acid tert-butyl ester oxalate, is converted to its free base by treatment with base followed by Boc deprotection of the amino group to give [(S)-1-(4-phenyl-1-H-imidazol-2-yl)-ethyl]-amine, compound (II), in pure form. The base can be any suitable base known to the skilled person, such as any suitable organic or inorganic base. Preferably, the base is an inorganic base, more preferably an alkali or alkaline carbonate or bicarbonate. More preferably, the base is a sodium carbonate. The base is dissolved in water and added to the suspension of compound (A-4a) in dichloromethane or a similar solvent such as tetrahydrofuran, diethyl ether, dimethyl ether or ethyl acetate.

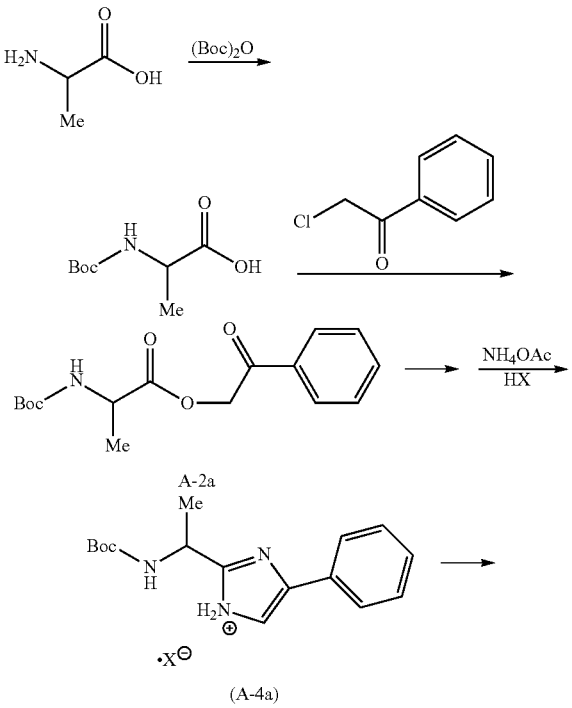

Scheme II

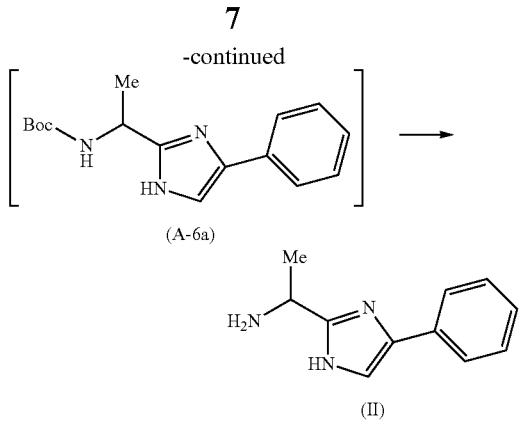

A distinct advantage of the process of the invention is that compound with formula (A-4a) is obtained in high yield and very pure form. Preferably, the compound is the oxalate salt of a compound with formula (A-4a). The oxalate salt of the compound with formula (A-4a) is obtained with purity in excess of 99% by HPLC. The compound further has a characteristic endothermic differential scanning calorimetric (DSC) peak in the range of 85 to 102° C., preferably in range of 91-95° C., more preferably 92-94° C., and even more preferably at about 93° C. In one embodiment, the compound is characterized by an differential scanning calorimetric endothermic peak at 93° C.

Compound with formula (A-4a) obtained by the process of the invention is further characterized by a powder x-ray diffraction pattern that comprises peaks with 2-theta values of about 9.05, 10.66, 13.3, 14.69, 16.78, 19.0, 20.76, 21.64, 24.84 and 25.69°. Preferably, the compound is characterized by an x-ray diffraction pattern as shown in FIG. 1. Preferably, the compound is the oxalate salt with formula (A-4a).

The novel oxalate salt of compound (A-4a) that is obtained by the process of the invention results in the formation of compound (II) in high yield and remarkable purity, without the requirement of further purification by liquid chromatography, which inevitably results in decreased yield. The process is further easily scalable, and thus useful on an industrial level.

The present invention will now be exemplified by the following non-limiting examples.

EXAMPLES

Example 1: Synthesis of of Boc-S-Alanine

In a cooled solution of L-alanine (100 g) in water (500 ml) and 1, 4-dioxan mixture (100 ml), sodium hydroxide (44.9 g) was added at 0-5° C. The resulting solution was stirred for 15 minutes at this temperature followed the dropwise addition of a solution of di-tert-butoxycarbonyl anhydride (257 g) in 1,4-dioxane (100 ml), while maintaining temperate at 0-5° C. The reaction mixture was stirred at room temperature for 12 to 15 hours, until completion. The reaction mass was cooled to 0-5° C. and ethyl acetate (800 ml) was added, followed by drop-wise addition of hydrochloric acid (112.3 ml). The organic layer was separated and the aqueous layer was then extracted with ethyl acetate (200 ml). Combined organic layers were washed with water and solvent was evaporated. The product was recrystallized in n-hexane (600 ml) to give 192.5 g (90.6%) Boc-alanine.

Example 2: Synthesis of Boc-S-Alanine Phenacylester

To a solution of Boc-S-Alanine (146.7 g) in dimethylformamide (500 mL) at 20-30° C. was added potassium carbonate (53.6 g), and the reaction mixture was stirred for 30 minutes at 20-30° C. Phenacyl chloride (100 g) was added to the reaction mixture and the resulting mixture was stirred until the reaction was complete (about 3-6 hours). After the reaction was completed, the reaction mass was cooled to 15-25° C., followed by addition of ethyl acetate (1000 ml) and water (1500 ml). The organic layer was separated and washed with water. The solvent was evaporated and the obtained product recrystallized in hexane (400 ml) to produce 193 g (81%) pure product with chiral purity 100%, HPLC purity 99.8%.

Example 3: Synthesis of [(S)-1-(4-phenyl-1-H-imidazol-2-yl)-ethyl]-carbamic acid tert-butyl ester oxalate salt A mixture of Boc-S-Alanine Phenacylester (340 g) and ammonium acetate (1313.86 g) in toluene (1750 ml) was heated to 95-105° C. for two to three hours. After the reaction was completed, the reaction mass was cooled to 40-45° C. and water (200 ml) was added. The organic layer was separated and distilled under reduce pressure. The resulting residue was dissolved in ethyl acetate (400 ml). Oxalic acid (139.5 g) was added to this solution at 20-30° C. and the suspension was stirred for two hours at 0-5° C., filtered and washed with ethyl acetate (150 ml). The product thus obtained was dried at 45-50° C. to give 491 g (95%) of [(S)-1-(4-phenyl-1-H-imidazol-2-yl)-ethyl]-carbamic acid tert-butyl ester oxalate salt with 99% purity.

The final product is characterized a powder X-ray diffraction (XRD) pattern as shown in FIG. 1. The XRD pattern shows the following main peaks as 2-theta values as indicated in the following table:

| Peak | 2-theta values |
|------|----------------|
| 1 | 9.05 |
| 2 | 10.66 |
| 3 | 13.3 |
| 4 | 14.69 |
| 5 | 16.78 |
| 6 | 19.0 |
| 7 | 20.76 |
| 8 | 21.64 |
| 9 | 24.84 |
| 10 | 25.69 |

Figure 2:
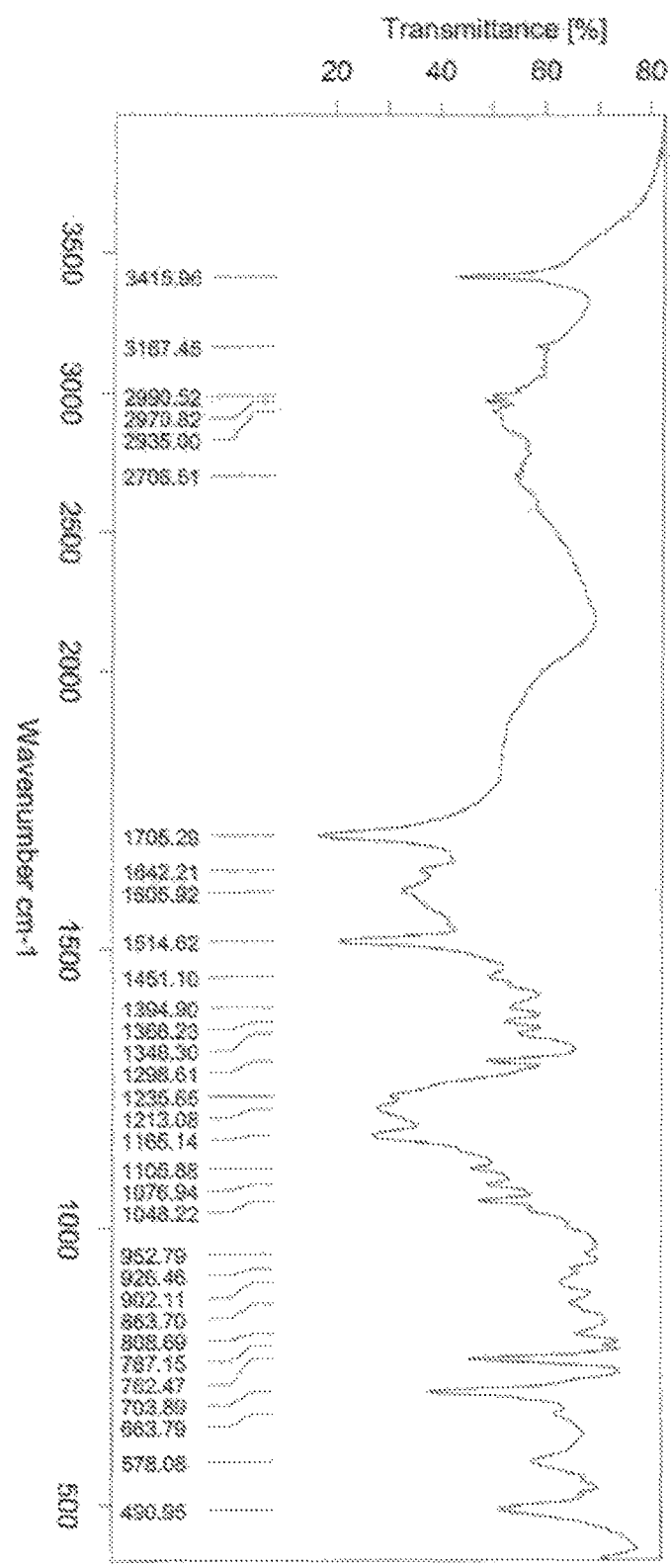
FIG. 2 shows an Infrared Spectrum (IR) of [(S)-1-(4-phenyl-1-H-imidazol-2-yl)-ethyl]-carbamic acid tert-butyl ester oxalate, as obtained by the process of the invention.
Figure 3:
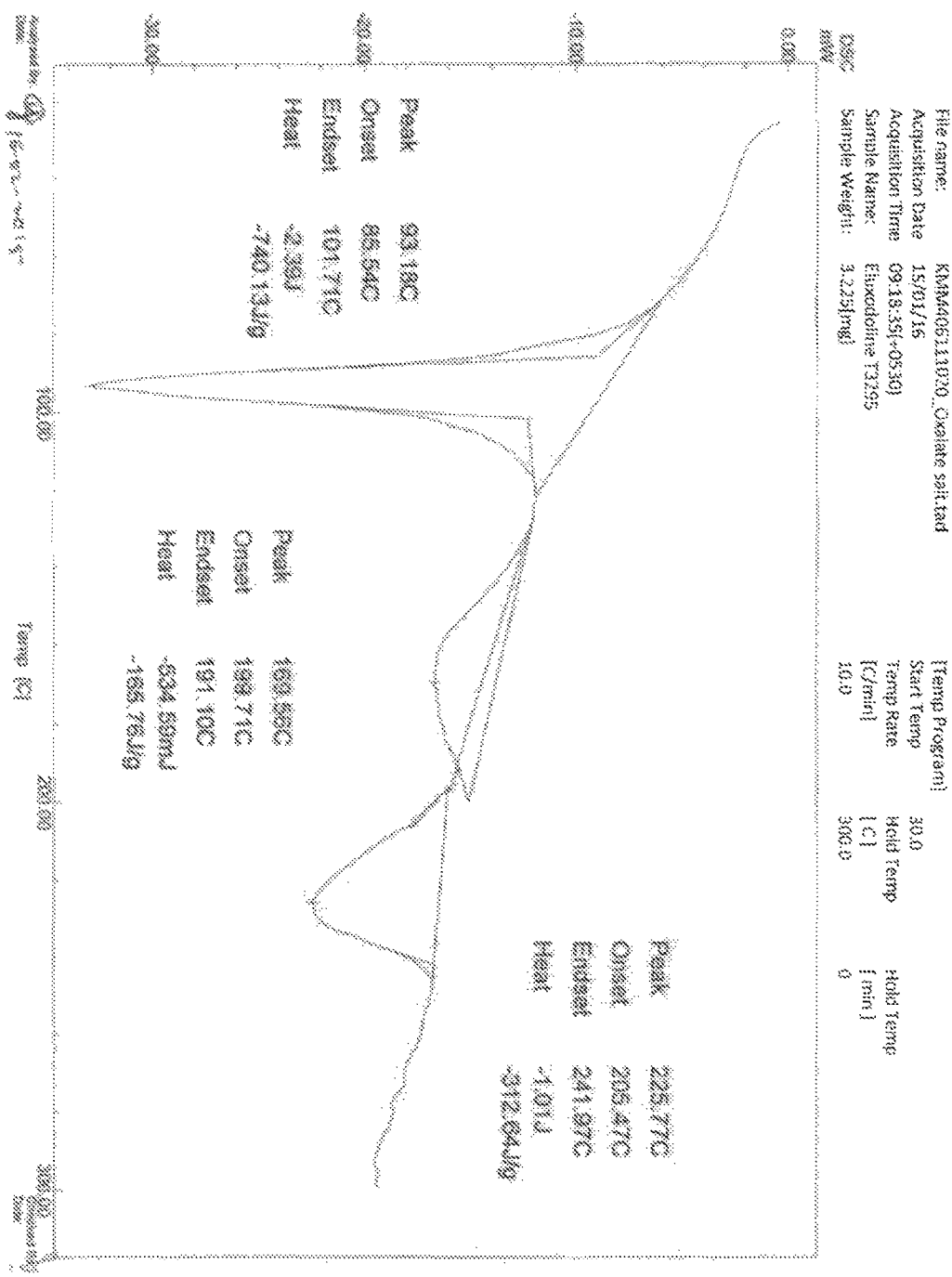
FIG. 3 shows results of Differential Scanning calorimetry (DSC) of [(S)-1-(4-phenyl-1-H-imidazol-2-yl)-ethyl]-carbamic acid tert-butyl ester oxalate, as obtained by the process of the invention.
Figure 4:
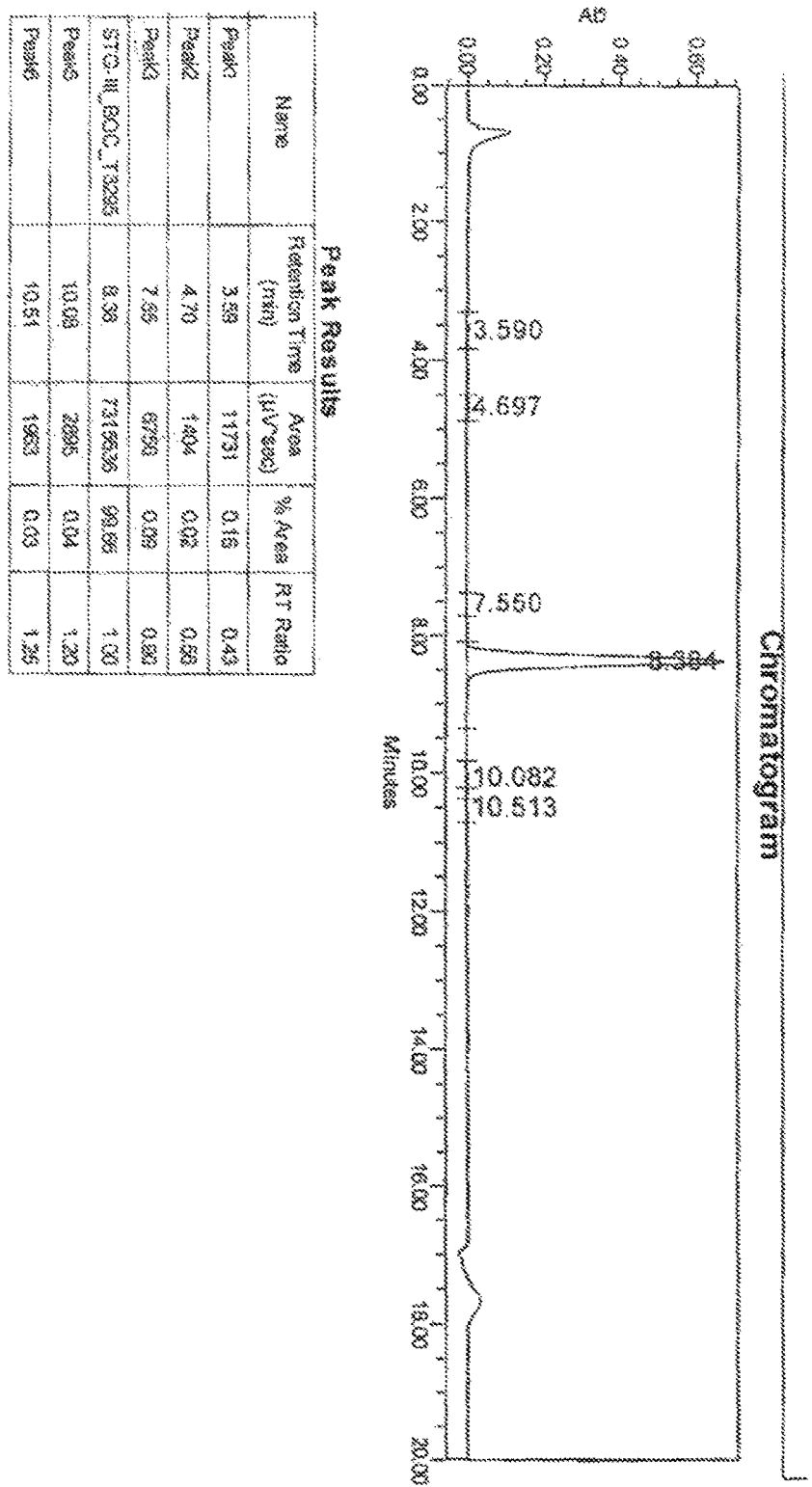
FIG. 4 shows results of HPLC analysis of [(S)-1-(4-phenyl-1-H-imidazol-2-yl)-ethyl]-carbamic acid tert-butyl ester oxalate, as obtained by the process of the invention.

The [(S)-1-(4-phenyl-1-H-imidazol-2-yl)-ethyl]-carbamic acid tert-butyl ester oxalate salt is further characterized by an Infrared Spectrum (IR) as shown in FIG. 2, a differential Scanning Calorimetry (DSC) with a major peak at around 93° C. as shown in FIG. 3, and has a purity by HPLC of at least 99.66%, as shown in FIG. 4.

Example 4: Synthesis of [(S)-1-(4-phenyl-1-H-imidazol-2-yl)-ethyl]-amine

An aqueous solution of sodium carbonate (5000 ml water and 456 g sodium carbonate) was added to solution of Boc-(S)-1-(4-phenyl-1-H-imidazol-2-yl)ethanamine oxalate salt (491 g) in dichloromethane (2000 ml). After stirring for two hours, organic layers ware separated and the aqueous layer was extracted with dichloromethane (600 ml). Combined organic layers were concentrated under reduce pressure. The obtained residue was dissolved in 5% methanolic hydrochloride solution (1500 ml). The solution was heated to 50-65° C. until completion of reaction. The reaction mixture was cooled to 10-15° C. and sodium carbonate (38 g) was added to the reaction mixture, followed by stirring for two hours. The solution was filtered and the filtrate concentrated to obtain 160 g (81%) of product [(S)-1-(4-phenyl-1-H-imidazol-2-yl)-ethyl]amine with 99.4% purity by HPLC and more than 99% chiral purity.

What is claimed is:

1. An oxalate salt of a compound with the formula

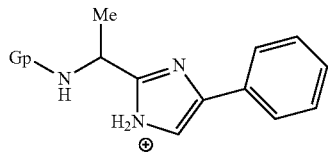

wherein Gp is an amino protecting group and thus Gp-NH in the formula is formed from the group consisting of 9-fluorenylmethyl carbamate (FMOC amide), t-butyl carbamate (BOC amide), benzyl carbamate, acetamide, trifluoroacetamide, phthalimide, benzylamine, triphenylmethylamine, benzylideneamine, and tosylamide.

2. The oxalate salt of claim 1, wherein Gp-NH is formed from t-butyl carbamate (BOC amide).

3. Crystalline [(S)-1-(4-phenyl-1-H-imidazol-2-yl)-ethyl]-carbamic acid tert-butyl ester oxalate.

4. The crystalline oxalate of claim 3 characterized by at least one of the following:
   a. Powder X-ray diffraction peaks with 2-theta values of 9.05, 10.66, 13.3, 14.69, 16.78, 19.0, 20.76, 21.64, 24.84 and 25.69°; and
   b. A differential scanning calorimetric thermogram with an endothermic peak at about 93° C.

* * * * *